United States Patent [19]

Mairesse et al.

[11] Patent Number: 5,573,655
[45] Date of Patent: Nov. 12, 1996

[54] ELECTROCHEMICAL CELL AND ITS USE IN THE SEPARATION OR ELECTROCHEMICAL EXTRACTION OF OXYGEN

[75] Inventors: Gaetan Mairesse; Jean-Claude Boivin, both of Villeneuve D'Ascq; Gilles Lagrange, Forges les Bains; Panayotis Cocolios, le Chesnay, all of France

[73] Assignees: L'Air Liquide, Societe Anonyme pour l'Etude et l'Exploitation des Procedes Georges Claude, Paris; Universite des Sciences et Technologies de Lille; Ecole National Superieure de Chimie de Lille, both of Villeneuve D'Ascq, all of France

[21] Appl. No.: 244,030

[22] PCT Filed: Sep. 13, 1993

[86] PCT No.: PCT/FR93/00871

§ 371 Date: Jul. 28, 1994

§ 102(e) Date: Jul. 28, 1994

[87] PCT Pub. No.: WO94/06544

PCT Pub. Date: Mar. 31, 1994

[30] Foreign Application Priority Data

Sep. 14, 1992 [FR] France ................... 92 10903

[51] Int. Cl.⁶ ........................................ C25B 1/02
[52] U.S. Cl. .................. 205/634; 205/635; 204/257; 204/295; 204/291; 429/33; 429/40
[58] Field of Search .................... 204/59 R, 129, 204/252, 291, 295, 283, 282; 429/33, 40; 205/634, 635

[56] References Cited

U.S. PATENT DOCUMENTS

| | | | |
|---|---|---|---|
| 4,675,260 | 6/1987 | Sakurai et al. | 429/218 |
| 4,789,561 | 12/1988 | Schafer et al. | 427/126.1 |
| 5,227,257 | 7/1993 | Abraham et al. | 429/33 |
| 5,273,628 | 12/1993 | Liu et al. | 204/59 R |

FOREIGN PATENT DOCUMENTS

| | | |
|---|---|---|
| 0 239 771 | 10/1987 | European Pat. Off. . |
| 0 438 902 | 7/1991 | European Pat. Off. . |
| 0 443 259 | 8/1991 | European Pat. Off. . |
| 91/01274 | 2/1991 | WIPO . |
| 91/06692 | 5/1991 | WIPO . |

*Primary Examiner*—Kathryn Gorgos
*Attorney, Agent, or Firm*—Burns, Doane, Swecker & Mathis, LLP

[57] ABSTRACT

The present invention relates to an electrochemical cell comprising a solid electrolyte which conducts $O^{2-}$ anions in contact with an anode and a cathode of identical or different composition, the solid electrolyte being comprised of a composition derived from $Bi_4V_2O_{11}$ of which at least one of the constituent cationic elements is substituted by at least one substituting element such that the gamma phase structural type of $Bi_4V_2O_{11}$ is maintained as well as the equilibrium of charges, at least one of the anode or of the cathode is a material containing at least one element of substitution of said composition derived from $Bi_4V_2O_{11}$, that element being in a metallic or cationic state. The invention equally relates to the use of the electrochemical cell with a view towards the separation or extraction of oxygen.

23 Claims, No Drawings 5,573,655

ELECTROCHEMICAL CELL AND ITS USE IN THE SEPARATION OR ELECTROCHEMICAL EXTRACTION OF OXYGEN

This is a 371 of PCT/FR 93/00871 filed Sep. 13, 1993 and published as WO94/06544 Mar. 31, 1994.

BACKGROUND OF THE INVENTION (i) Field of the Invention

The present invention has for its object an electrochemical cell comprising a solid electrolyte, an anode and a cathode as well as the use of this electrochemical cell with a view towards the electrochemical separation of gases from a mixture of at least one gas and of oxygen or with a view towards the extraction of oxygen from a molecule containing oxygen, such as CO, $CO_2$ and $H_2O$.

(ii) Description of Related Art

It is known that some solid electrolytes, comprised for example of derivatives of oxides of zirconium, yttrium, bismuth or cerium, containing or not containing dopants such as ytterbium or calcium, can be used as conductors of $O^{2-}$ ions, when they are subjected to an electric field and/or a difference of partial pressure of oxygen. These derivatives typically posses the same base structure derived from the so-called structure of the fluorine type presenting oxygenated gaps. They permit a conduction of $O^{2-}$ ions which is essentially tri-dimensional.

Besides, solid electrolyte conductors for $O^{2-}$ anions have been described in U.S. Pat. No. 5,227,257 the teachings of which are totally incorporated herein by reference. These electrolytes are comprised of a composition derived from $Bi_4V_2O_{11}$, of which at least one of the constituent elements is substituted by one or several substituting elements chosen of the kind such that the structural type of the gama phase of $Bi_4V_2O_{11}$ is maintained as well as the equilibrium of the charges. This type of solid electrolyte presents a lamellar structure in which the mechanism of conduction of the $O^{2-}$ ions is essentially bi-dimensional. Thus, the compositions derived from $Bi_4V_2O_{11}$ are also distinguished from those typically used in the making up of solid electrolytes by their chemical nature, their crystalline structure and their mode of conducting $O^{2-}$ ions.

Some solid electrolytes comprised of compositions derived from $Bi_4V_2O_{11}$ possess the remarkable property of permitting an artionic conductivity of $10^{-3}\Omega^{-1}cm^{-1}$ to 200° C., which is of the order of one hundred times superior to the performances of materials currently on the market. Such classical materials are themselves inoperative at temperatures less than 300° C. In order to attain an artionic conductivity on the order of $10^{-3}\Omega^{-1}cm^{-1}$, it is necessary to take them to temperatures greater than about 600° C.

It has, however, been observed by the applicants that some classical electrodes, notably those of silver base, deposited on the electrolyte in the form of a lacquer for example, lead when they are associated with a solid electrolyte comprised of a composition derived of $Bi_4V_2O_{11}$, to a rapid deactivation of the electrochemical cell. Such a deactivation is not produced when the solid electrolyte is comprised, for example, of a classical stabilized zirconium.

It is well understood that such a deactivation of the electrochemical cell is not compatible with exploitation on an industrial scale. Without being bound to a theoretical explanation, the applicants have attributed such deactivation to a chemical reaction between one or several of the constituent elements of the electrolyte derived from $Bi_4V_2O_{11}$ and the electrode of silver base.

Besides, it has been observed that some electrochemical cells formed from a solid electrolyte comprised of a composition derived from $Bi_4V_2O_{11}$ and of classical electrodes, when they are employed with a view towards the separation of oxygen from air, do not permit, or very weakly, such a separation.

SUMMARY AND OBJECTS OF THE INVENTION

The applicants have pursued their research in order to perfect an electrochemical cell whose solid electrolyte is comprised of a composition derived from $Bi_4V_2O_{11}$, not rapidly being deactivated, permitting exploitation on an industrial scale, notably with a view towards the efficient separation of oxygen from air or from another mixture of gas containing oxygen, as well as the extraction of oxygen from a molecule containing oxygen.

The applicants have thus perfected an electrochemical cell comprised of a solid electrolyte, an anode and a cathode, the electrolyte being comprised of a compound derived from $Bi_4V_2O_{11}$ and the anode and the cathode being chosen of the kind to be compatible and to not react chemically with such a compound.

The present invention thus, relates to an electrochemical cell comprised of a solid electrolyte conductive for $O^{2-}$ anions in contact with an anode and a cathode of identical or different composition, said solid electrolyte being comprised of a composition derived from $Bi_4V_2O_{11}$ of which at least one of the constituent cationic elements is substituted by at least one substituting element chosen such that the gamma phase structural type of $Bi_4V_2O_{11}$, as well as the equilibrium of the charges is maintained; said electrochemical cell being characterized in that at least one of the anode or the cathode is a material containing at least one substituting element of said composition derived from $Bi_4V_2O_{11}$; this element being in a cationic or metallic state. The constituent material or materials of the anode and of the cathode must, by definition, be conductive electronic materials.

DETAILED DESCRIPTION OF PREFERRED EMBODIMENTS

The applicants have in effect been able to observe that when at least one of the anode or of the cathode contains one of the substituting elements or, if necessary, the unique substituting element of the composition derived from $Bi_4V_2O_{11}$ comprising the solid electrolyte, the electrochemical cell not having been deactivated and permitting a prolonged functioning over time notably with a view towards the electrochemical separation of oxygen from a gaseous mixture containing oxygen or with a view towards the extraction of oxygen contained in a molecule. It will be understood that the constituent material of the anode and/or of the cathode is chosen of the type such that it will not react chemically with the solid electrolyte.

According to a one embodiment of the invention, the solid electrolyte is a composition derived from $Bi_4V_2O_{11}$ which corresponds to the formula (I):

$$(Bi_{2-x}M_xO_2)(V_{1-y}M'_yO_2) \tag{I}$$

in which

M represents one or several substitution elements of Bi, chosen from among those having an oxidation number less than or equal to 3, M' represents one or several substitution elements of V chosen among those having an oxidation number less than, equal to or superior to 5, the limits of the values for x, y and therefore z being a function of the nature of the substituting elements M and M'.

When such an electrolyte is placed into operation, at least one of the anode or of the cathode is an electronically conductive material containing at least one element M and/or M' in a metallic or cationic state.

In a preferred manner, said solid electrolyte is a composition derived from $Bi_4V_2O_{11}$ which corresponds to the formula (II):

$$(Bi_2O_2)(V_{1-y}M'_yO_z) \quad\quad (II)$$

in which M' and z are as defined above, y not being 0, and at least one of the anode or the cathode is an electronically conductive material containing at least one element M' in a metallic or cationic state. The symbol M' is advantageously selected among the alkaline metals, alkaline earths, transition elements, notably elements of groups III to V of the Periodic Table and the rare earths.

Preferably, M' is chosen among zinc, copper, nickel, cobalt, iron, magenese and cadmium.

The solid electrolyte can also be comprised of a composition derived from $Bi_4V_2O_{11}$ where only the bismuth atom is partially substituted by one or several elements. Such a composition corresponds to the formula (III):

$$(Bi_{2-x}M_xO_2)(VO_z) \quad\quad (III)$$

in which M and z are as defined above and x is not equal to 0. Preferably, M is a rare earth, such as lanthanum.

When such a solid electrolyte is placed in operation, at least one of the anode or the cathode is an electronically conductive material containing at least one element M in a metallic or cationic state.

It is still possible that the solid electrolyte is a composition derived from $Bi_4V_2O_{11}$ of the formula (I) described above, in which x and y are not 0. At least one of the anode and the cathode is thus of an electronically conductive material containing at least one dement M and at least one dement M' in a metallic or cationic state.

Preferred solid electrolytes within the scope of the invention are those of a composition derived from $Bi_4V_2O_{11}$ containing only a single element of substitution M or M', at least one of the anode and the cathode thus being of a material containing a single element M or M' in metallic or cationic state, M and M' being as defined above.

At least one of the anode or the cathode according to the invention can besides be equally of an electronically conductive or ionically conductive material, for instance of a mixed electronic and ionic conductive material, containing at least one element of substitution of the composition derived from $Bi_4V_2O_{11}$ in a cationic state.

Such a mixed electronic and ionic conductive material can be a ceramic such as the manganites, cobaltites or ferrites of lanthanum doped with strontium, cerium or thorium, the compounds of the formula (IV):

$$YBa_2Cu_3O_{7-x'} \quad\quad (IV)$$

where x' ranges between 0 and 1, the oxides of bismuth or the oxides of cerium doped by one or two cations, the oxides of vanadium and strontium, the oxides of vanadium and lead, the oxides of calcium and titanium of formula (V):

$$CaTi_{1-x''}M^1_{x''}O_{3-t} \quad\quad (V)$$

where $M^1$ is a transition element and x" and t have limiting values which are a function of the nature of $M^1$.

The compositions derived from $Bi_4V_2O_{11}$ such as described above can be prepared according to the process described in patent application U.S. Pat. No. 5,227,257.

These compositions, generally in the form of a powder, are advantageously put in form for being used as a solid electrolyte in the electrochemical cell according to the invention.

Thus, the solid electrolyte may or may not be present in the form of a supported tube by a porous support like a tube of a ceramic such as alumina, a sintered porous metal or a manganite of lanthanum doped with strontium for example, of a disk, of a plate or of a multi-layered alveole. The thickness of the solid electrolyte can range from between 0.001 and 2 mm and preferably between 0.01 and 1 min. The anode and the cathode are generally disposed on two faces opposite the solid electrolyte.

The anode and/or the cathode according to the invention can be present in the form of a layer of a plate or a grid of an electronic conductive material, adhering to the surface of the solid electrolyte. When the anode and/or the cathode according to the invention are present in the form of a layer adhering to the surface of the solid electrolyte, that layer can be applied according to different methods. Among these methods, there can be cited the application of a layer by painting using a brush, silk screen painting, soaking, aerosol projection, plasma aerosol projection, chemical deposition at vapor state (CVD), deposition under a vacuum (PVD) including evaporation under a vacuum and sputtering, chemical deposition in solution without employing an electrical current, chemical deposition in solution under the influence of a difference of potential. According to the chosen method, said electronic conductive material can be present in admixture with different excipients such as solvents or binders chosen of the type which are easily eliminated from the surface of the solid electrolyte.

Thus, if the chosen method is the application by painting, said constituent material of the layer is mixed with solvents and organic binders which can be eliminated by an appropriate thermal treatment.

According to the chosen method, said material, following its deposition on the electrolyte, can be sintered at temperatures which can range between 20° and 850° C.

It can be advantageous, notably when the anode and/or the cathode according to the invention is a mixed electronic and ionic conductor material, to place said anode and/or cathode in contact with an essentially conductive or uniquely electronic compound which may or may not contain a substitution dement of the composition derived from $Bi_4V_2O_{11}$.

Such a compound can be present in the form of a layer, in a grid or a plate superposing said anode and/or cathode.

Such an electronic conductive compound can comprise an element in the metallic state or an alloy of such element, said dement advantageously being chosen among the transition elements, such as the lanthanides and actinides such as lanthanum, cerium, ytterbium or niobium or an element of groups $III_b$, $IV_b$, $V_b$, $VI_b$, or $VII_b$ of the Periodic Table.

In a still more advantageous manner, said dement is chosen among iron, cobalt, nickel, copper, zinc and gold.

When said electronic conductive compound is present in the form of a layer, it can be superposed to the anode and/or the cathode by means of one of the methods described above for which relates to the application of a layer comprising the anode and/or the cathode.

The invention equally relates to the use of the electrochemical cell described above for the construction of oxygen gauges and amperometric meters, combustible calls, installations for the electrochemical separation of gas, of oxygen, from a mixture of gas containing oxygen or an installation for the electrochemical extraction of oxygen from a molecule containing oxygen.

With respect to the installation for the electrochemical separation of oxygen in which the electrochemical cell of the invention can be employed, there can be cited the work described in Solid State Ionics 28–30 (1988), 524–528 by Dumelie M. et at.

In this type of installation, the electrochemical cell according to the invention notably permits the separation of oxygen from a mixture of oxygen and nitrogen such as air or a mixture of argon and oxygen.

With respect to the installations for the electrochemical extraction of oxygen from a molecule containing oxygen, there can be cited the work described in Japanese patent applications 85/172360 and 85/172359.

In this type of installation, the electrochemical cell according to the invention permits extracting oxygen from carbon monoxide or from carbon dioxide. Installations of the same type permit the use of the electrochemical cell according to the invention to extract oxygen from water, from $NO_x$ or $SO_x$.

The examples which follow have as their goal the illustration of the present invention.

EXAMPLE 1 (ACCORDING TO THE INVENTION)

There is described an installation for the electrochemical separation of oxygen from air in the following manner:

1) There is prepared a solid electrolyte in the form of a disk starting from a powder of a composition derived from $Bi_4V_2O_{11}$ of formula $Bi_2V_{0.9}Ni_{0.1}O_{5.35}$ (BiNi-$Vo_x$). In order to do this, the powder is ground in such manner that the average diameters of the grains is about 6 microns, the granulometry varying from 0.3 to 15 microns. The disk is obtained by pressing by applying to the ground powder a force on the order of 6 tons. It has a surface of 2 $cm^2$ and a thickness of 1.2 mm.

2) The disk is then sintered at 820° C. for five hours in an atmosphere of air of the kind so as to obtain a product which is mechanically resistant and impermeable to gases.

3) On a part of each of the surfaces of the disk, there is deposited with the aid of a brush a layer of a lacquer having a nickel base.

This deposit is dried for an hour at 150° C. and the solvents and organic binders are eliminated by bringing the temperature to 350° C. for another hour. Then the electrodes of the disk are baked at 600° C. for about 1 minute under an inert atmosphere ($N_2$).

4) The solid electrolyte disk provided on each of the surfaces of the electrode forms a cell which is deposited on the section of a conductive tube of stainless steel. In order to maintain the disk in a stable manner on the section of the stainless steel tube, there is applied an adhesive cement impermeable to gas and electrically isolated on the section of the disk and on an external part of said tube. The electrical contact on the anionic side is comprised of the stainless steel tube and the electrical contact on the cathodic side is assured by an external metallic rod, one of the extremities of which is in contact with the nickel electrode.

In functioning for the electrochemical separation of oxygen from air, the cathodic side of the disk is put in contact with air. Pure oxygen is recovered in the stainless steel tube, on the anionic side of the cell.

The stainless steel tube and the metallic rod are linked to an electrical generator. The cell is subjected to a temperature of 500° C. The applied intensity to the terminals of the cell is 0.3 A, which corresponds to a potential of 10 volts for the length of the experiment. The cell, therefore, function under a current density of 1493 $A/m^2$.

The production of pure oxygen was from 0.1 ml/min going back to unity of surface (1 $cm^2$) for a duration of 70 minutes, after which the nickel layer on each of the faces of the pastille remains intact.

EXAMPLE 2 (ACCORDING TO THE INVENTION)

There is described an installation similar to that of example 1 but where the solid electrolyte disk has a surface of 2 $cm^2$ and the layer of nickel on each of the faces of the pastille is replaced by a grid of nickel having a thickness of 0.45 mm and of which the cavities have a diagonal of 1 mm.

With a view towards the production of pure oxygen starting from air, the installation was subjected to a temperature of 480° C. and there is applied an intensity of 0.3 A to the terminals of the cell. This intensity corresponds to a potential of 18.2 volts for the duration of the experiment. This cell therefore functioned under a current density of 1493 $A/m^2$.

The production of pure oxygen in these conditions was 0.17 ml/min brought back to the unity of surface (1 $cm^2$) for a duration of 30 minutes.

EXAMPLE 3 (COMPARATIVE)

There is described an installation similar to that of example 1, but where the disk of the cell has a surface of 2.27 $cm^2$ and a thickness of 1.1 mm, and where the electrode and the cathode are silver instead of being nickel.

With a view towards the production of pure oxygen starting from air, the cell is subjected to a temperature of 420° C.

The applied intensity to the terminals of the cell is 0.3 A. This intensity corresponds to a potential of 11 V. That cell has therefore functioned under a current density of 1322 $A/m^2$. The production of pure oxygen in these conditions was from 0.01 ml/min going back to unity of surface (1 $cm^2$) for a duration of 10 minutes. During this very short delay in the functioning, the silver of the electrodes apparently reacted with the electrolyte to form a material of a different nature from that previously which was inactive for the separation of oxygen from air.

We claim:

1. Electrochemical cell comprising:
   a solid electrolyte which conducts $O^{2-}$ anions comprising a $Bi_4V_2O_{11}$ composition wherein at least one of Bi and V is substituted by at least one substituting element which maintains gamma structural phase and charge equilibrium of said $Bi_4V_2O_{11}$;
   an anode and a cathode, of compositions identical to or different from each other in contact with said electrolytic solid, at least one of said anode and cathode being an electrically conductive material and including one of said substituting elements, wherein this element is in a metallic or cationic state.

2. Electrochemical cell according to claim 1 wherein the $Bi_4V_2O_{11}$ composition corresponds to the formula (I):

$$(Bi_{2-x}M_xO_2)(V_{1-y}M'_yO_z) \quad (I)$$

in which:
M represents one or several substitution elements of Bi, chosen from among those having an oxidation number less than or equal to 3,
M' represents one or several elements of substitution of V,
x, y and z are a function of the nature of the substituting elements M and M',
at least one of the anode or the cathode is a conductive electronic material including at least one element M, at least one element M' or at least one element M and M' in a metallic or cationic state.

3. Electrochemical cell according to claim 2 wherein the $Bi_4V_2O_{11}$ composition corresponds to the formula (II):

$$(Bi_2O_2)(V_{1-y}M'_yO_z) \quad (II)$$

in which, y is not zero, and at least one of the anode or the cathode is a conductive electronic material including at least one element M' in a metallic or cationic state.

4. Electrochemical cell according to claim 3 wherein M' is an alkaline metal, an alkaline earth, a transition element or a rare earth element.

5. Electrochemical cell according to claim 4 wherein M' is a transition element selected from the group consisting of elements of groups III to V of the Periodic Table.

6. Electrochemical cell according to claim 2 wherein the $Bi_4V_2O_{11}$ composition corresponds to the formula (III):

$$(Bi_{2-x}M_xO_2)(VO_z) \quad (III)$$

which x is not zero and at least one of the anode or the cathode is a conductive electronic material including at least one element M in a metallic or cationic state.

7. Electrochemical cell according to claim 6 wherein M represents a rare earth metal.

8. Electrochemical cell according to claim 7 wherein M is lanthanum.

9. Electrochemical cell according to claim 2 wherein in the formula (I), x and y are not zero.

10. Electrochemical cell according claim 2 wherein the $Bi_4V_2O_{11}$ composition includes only a single element of substitution M or M' and at least one of the anode or the cathode is an electronic conductive material including a single element M or M' in a metallic or cationic state.

11. Electrochemical cell according to claim 10 wherein at least one of the anode or the cathode is a mixed electronic and ionic conductive material including at least one element of substitution of the $Bi_4V_2O_{11}$ composition in a cationic state.

12. Electrochemical cell according to claim 11 wherein said mixed electronic and ionic conductive material is a ceramic selected from the group consisting of (a) manganites, cobaltites or ferrites of lanthanum doped with strontium, cerium or thorium, (b) compounds of formula (IV):

$$YBa_2Cu_3O_{7-x'} \quad (IV)$$

where x' ranges between 0 and 1, (c) oxides of bismuth or oxides of cerium doped by one or two cations, (d) oxides of vanadium and strontium, (e) oxides of vanadium and lead, and (f) oxides of calcium and titanium of formula (V):

$$CaTi_{1-x''}M^1_{x''}O_{3-t} \quad (V)$$

where $M^1$ is a transition element and x" and t have values which are limited as a function of the nature of $M^1$.

13. Electrochemical cell according to claim 1 wherein at least one of the anode and the cathode are present in the form of a layer, a plate or a grid adhering to a surface of the solid electrolyte.

14. Electrochemical cell according to claim 1 wherein at least one of the anode or the cathode is a material including at least one element of substitution the $Bi_4V_2O_{11}$ composition, wherein said material is in contact with an essentially or uniquely electronic conductive compound optionally including an element of substitution of the $Bi_4V_2O_1$ composition.

15. Electrochemical cell according to claim 14 wherein said electronic conductive composition is a layer, a grid or a plate superposed to at least one of the anode and the cathode.

16. Electrochemical cell according to claim 14 wherein said essentially conductive electronic compound is an element in a metallic state or an alloy of such element in metallic state.

17. Electrochemical cell according to claim 16 wherein said element in metallic state is a transition element.

18. Electrochemical cell according to claim 17 wherein said transition element is gold, nickel, iron, cobalt, copper or zinc.

19. Method for electrochemical separation of oxygen contained in a gaseous admixture comprising contacting said gaseous admixture with the electrochemical cell according to claim 1 and recovering oxygen from said cell.

20. Method according to claim 19 wherein said gaseous admixture is a mixture of nitrogen and oxygen or a mixture of argon and oxygen.

21. Method according to claim 19 wherein said gaseous admixture from which oxygen is separated is air.

22. Method for electrochemical extraction of oxygen from a molecule including oxygen comprising contacting said molecule with the electrochemical cell according to claim 1 and separating oxygen from said molecule.

23. Method according to claim 22 wherein said molecule including oxygen is water, carbon dioxide, carbon monoxide, $NO_x$ or $SO_x$.

* * * * *